United States Patent [19]

Weber et al.

[11] Patent Number: 5,219,659
[45] Date of Patent: Jun. 15, 1993

[54] SUTURE MATERIAL MADE OF SYNTHETIC RESIN MONOFIL

[75] Inventors: Josef Weber, Hennef; Paul Spielau, Troisdorf-Eschmar; Jurgen Fenske, Leverkusen; Hans-Jürgen Schrick, Troisdorf-Eschmar; Gerhard M. Krahmer, Auf der Hedwigshöhe 4C, 5064 Rösrath 3, all of Fed. Rep. of Germany

[73] Assignee: Gerhard M. Krahmer, Rosrath, Fed. Rep. of Germany

[21] Appl. No.: 235,823

[22] Filed: Aug. 15, 1988

Related U.S. Application Data

[63] Continuation of Ser. No. 942,794, Dec. 17, 1986, abandoned, which is a continuation of Ser. No. 707,502, Mar. 4, 1985, abandoned, which is a continuation of Ser. No. 518,653, Jul. 29, 1983, abandoned.

[30] Foreign Application Priority Data

Jul. 30, 1982 [DE] Fed. Rep. of Germany ....... 3228428

[51] Int. Cl.$^5$ .......................... C08F 14/22; D02G 3/00
[52] U.S. Cl. ...................................... 428/397; 526/255
[58] Field of Search .......................... 526/255; 428/397

[56] References Cited

U.S. PATENT DOCUMENTS

| | | | |
|---|---|---|---|
| 3,707,592 | 12/1972 | Ishii et al. | 526/255 |
| 4,034,763 | 7/1977 | Frazier | 606/226 |
| 4,052,550 | 10/1977 | Chion et al. | 526/255 |
| 4,339,499 | 7/1982 | Tappe et al. | 428/373 |
| 4,564,013 | 1/1986 | Tilenfeld et al. | 128/335.5 |

FOREIGN PATENT DOCUMENTS

| | | | |
|---|---|---|---|
| 0037939 | 7/1984 | European Pat. Off. | |
| 1048088 | 11/1966 | United Kingdom | 128/355.5 |

OTHER PUBLICATIONS

Abstract of Gebrauchmuster 8221647 Nov. 25, 1982.

*Primary Examiner*—Thurman K. Page
*Assistant Examiner*—Peter F. Kulkosky
*Attorney, Agent, or Firm*—Antonelli, Terry, Stout & Kraus

[57] ABSTRACT

A suture material is made of a monofil of polyvinylidene fluoride which is drawn at a ratio of from 1:3 to 1:8 and which exhibits improved properties of elongation and elasticity.

8 Claims, 2 Drawing Sheets

SUTURE MATERIAL MADE OF SYNTHETIC RESIN MONOFIL

This application is a continuation of application Ser. No. 942,794, filed Dec. 17, 1986, which is a continuation of application Ser. No. 707,502, filed Mar. 4, 1985 which is a continuation of application Ser. No. 518,653, filed Jul. 29, 1983 all now abandoned.

This invention relates to suture material made of synthetic resin monofil.

Various fiber-forming materials are utilized for suture material, imparting their characteristic application possibilities to the thus-produced suture materials. The prior art comprises, on the one hand, the resorbable suture materials, such as chromic catgut, iodine catgut, plain catgut, and, on the other hand, the suture materials that cannot be resorbed, made of linen thread, cotton thread, silk, polyamides, polyesters, polyolefins, polyglycolic acid, tantalum, or steel.

The excellent properties displayed, for example, by silk as a suture material are high tear strength, suppleness, good knottability, and nonresorbability. Disadvantages include a wick effect, leading to the consequence of rejection by body tissue, and degradation of the suture material in the tissue and concomitant reduction in strength of the tissue seam. Linen thread exhibits similar drawbacks and advantages as silk, but it has yet remained popular for a very long time on account of its lower price.

An overview of the various suture materials and their advantages and drawbacks, as well as possibilities for their use can be found, for example, in P. F. Nockemann, *Die chirurgische Naht* (Sutures), Georg Thieme publishers, Stuttgart, N.Y., 1980.

Suture materials made of synthetic resins surpass suture materials of natural fibers and also catgut, in their properties in many respects. The most prominent property is their markedly higher tear strength. With regard to this factor, synthetic resin threads are surpassed only by metallic threads. In this connection, threads of a synthetic resin, in contrast to threads of natural substances, retain their strength almost unchanged even within the tissue.

For example, the tear strength of polyamide threads is 30% above that displayed by silk or ply yarn. Polyester threads have an even higher tear strength.

Besides the tear strength, depending on the thickness of the thread and being a yardstick for the knotting strength of the suture material, other significant factors for the reliability of the knot are surface characteristics, elasticity, and swellability. Furthermore, the properties of sterility and tissue compatibility must definitely be present.

The properties of high tear strength with simultaneous suppleness are of special advantage in synthetic resin threads. However, suppleness is coupled with high elasticity. A high elasticity, paired with high tear strength, represents a substantial disadvantage in synthetic monofil suture materials. The high elasticity of the synthetic resin threads proves to be deleterious when the surgeon has to tie knots, because he can guess the correct seam tension only with difficulties. Moreover, there is the danger that the cut-off ends of the thread, elongated during tightening, will slip back into the knot, thus opening the knot. This possible lack of knot safety requires a special knotting technique in all synthetic resin threads, to a greater or lesser extent. On account of the elastic extensibility, the threads must be pulled especially strongly before and during knotting. This, on the other hand, due to the high thread strength, is still possible with forces at which other threads would already be torn apart. However, the tissue seized along the suture is, thus, readily placed under excessively high pressure so that it is damaged.

In order to improve handling ability and to reduce the elongation of suture materials made of synthetic resin, multifilament threads have, thus, also been developed. Although a braided or multifilament thread is more supple than a monofil, it does exert a certain sawing effect on the tissue when used as a suture material. Therefore, in many cases, this disadvantageous roughness of multifilaments is counteracted by the application of an additional smoothing agent.

The invention is based on the object of providing a monofil suture material of a synthetic resin which exhibits low elongation and, thus, improved handling capacity.

This object has been attained by the invention in that it provides a stretched synthetic resin monofil of polyvinylidene fluoride (PVDF) as a suture material. It has been a surprise that stretched PVDF monofils are suitable as suture material and are not hindering the curing of wounds, i.e. they do not affect the medical treatment.

The monofilaments of PVDF according to this invention possess high tear strength and suppleness, but exhibit, as compared with known synthetic resin monofils, like polypropylene, which are used as suture material lower elasticity and, thus, lower elongation, which is a great advantage for the inventive suture material. This combination of properties improves handling as suture material. Furthermore, such monofilaments of PVDF are distinguished, for example, over materials of polypropylene by a reduced tendency to split.

Accordingly, the thread of this invention is better in handling in knot retention.

The monofil thread can be dyed with a suitable colorant to distinguish it from other materials. Preferably the dye pigment or dyestuff are added during compounding of the raw material for extrusion. The polyvinylidene fluoride monofil to be suitable for the use of this invention can be extruded for instance according to the process described in U.S. Pat. No. 4,264,555 at diameters of 0.2 to 2 mm for the unstretched monofil and then to be followed by a stretching process at an axial draw ratio of 1:3 to 1:8, preferably 1:3 to 1:6. The thread thickness of the stretched monofilament ranges preferably between 0.07 and 0.5 mm. The material can be optimized with respect to its strength by setting the degree of crystallinity, for example, by means of the cooling conditions after extrusion of the monofilament, whereby a gradual cooling or tempering at about 135° C. leads to highly crystalline material. The process for producing a monofil in accordance with the invention provides that a monofil is extruded at a melt temperature of PVDF of 240° to 350° C., preferably between 250° and 280° C., and cooled to a temperature between 125° and 145° C. and is axially stretched at this temperature, at a rate of preferably 1:3 to 1:6, whereupon this monofil is cooled to room temperature. Knot tear strength and elongation at rupture of knotted thread can be determined as a function of the degree of drawing (stretching), and can be appropriately adjusted, whereby the polyvinylidene fluoride monofil of this invention, as suture material, exhibits an axial draw ratio of 1:3 to 1:8, preferably 1:4 to 1:6 to receive the quality desired for the suitability as suture material. An essential point is that the tear strength or knot tear strength which, of course, depends on the thickness of the monofil, satisfies the requirement to be met by the suture material, laid down in the national medical standards resp. European Pharmakopöe.

stable and durable seat of the knot, which does not loosen or disband. The improvement of the PVDF monofil according to the invention compared with polypropylene monofil with regard to elongation at rupture and tear strength is remarkably.

TABLE 1

| Designation of Material | Thickness (mm) | Tear Strength (N) | Elongation at Rupture (%) | Knot Elongation at Rupture (%) |
| --- | --- | --- | --- | --- |
| PVDF Monofil Thickness (mm) | | | | |
| 0.14 | 0.152 | 12.5 (12.0–13.1) | 15 (14–16) | 8.8 |
| 0.19 | 0.196 | 22.4 (20.7–24.1) | 15 (14–16) | 8.8 |
| 0.27 | 0.279 | 45.6 (33.2–39.2) | 15 (13–16) | 11.4 |
| 0.33 | 0.326 | 60 (55.1–62.5) | 16 (15–17) | 14.4 |
| 0.38 | 0.37 | 81.5 (77.5–86) | 16 (15–18) | 7.8 |
| Polypropylene Monofil Thickness (mm) | | | | |
| 0.7 metric, 6-0 | 0.100 | 4.3 | 35 | 30 |
| 1.5 metric, 4-0 | 0.185 | 11.7 | 40 | 26 |
| 2 metric, 3-0 | 0.25 | 20.5 | 30 | 26 |
| 3 metric, 2-0 | 0.315 | 33 | 35 | 22 |

The knot elongation at rupture is, in the monofils of this invention, only 8–20%, preferably 8–18%. Thus, this knot elongation at rupture is lower by 50% than in the comparable monofils for suture material made of polyolefins or polyamides. In case the elongation of rupture is too high, the security of knot is not given during knotting and thereafter, since the knot may open by back drawing of the monofil. Therefore a low value of elongation at rapture is very important for suture material.

Moreover, results obtained from tests show that PVDF monofils exhibit a very good tissue compatibility and do not cause inflammation.

The suture material of this invention will be further understood from the following detailed description and the accompanying drawings wherein:

BRIEF DESCRIPTION OF THE DRAWINGS

In FIG. 1, a PVDF monofil 10 is shown in a knotted configuration. The PVDF monofil exhibits a very high tear strength knot tear strength, slip strength, relatively low elongation at rupture, very high suppleness, smooth surface, no splitting, and good diameter constancy. The following Tables 1 and 2 list the measured values for knot tear strength, tear strength, and elongation at rupture of PVDF monofils according to this invention and of commercially available polypropylene (PP) monofils of various thicknesses.

The measured properties have the following meanings:

| | |
| --- | --- |
| knot tear strength: | the knot is made and tear strength measured according to DIN 53 816, resp. European Pharmakopöe standard |
| tear strength: | according to DIN 53 816; |
| elongation at rupture: | according to DIN 53 455; |
| knot elongation at rupture: | the knot is made and then measured according to DIN 53455. |

Table 1 shows that PVDF monofils processed for the invention have a very low elongation rupture, which is important for the suture material to receive a good and

TABLE 2

| | | Knot Tear Strength | |
| --- | --- | --- | --- |
| Designation of Material | Thickness (Measured Value) (mm) | Measured Value (N) | Desired Value (N) |
| PVDF Monofil Thickness (mm) | | | (for Polyamide) |
| 0.14 (1.5 metric) | 0.152 (0.145–0.160) 1) | 4.8 (4.2–5.3) | 3.0 |
| 0.19 (2.0 metric) | 0.196 (0.192–0.204) 1) | 7.1 (7.3–9.0) | 6.0 |
| 0.27 (2.5 metric) | 0.279 (0.265–0.295) 1) | 15.7 (14.4–17.0) | 8.0 |
| 0.33 (3.0 metric) | 0.326 (0.295–0.365) 1) | 24.9 (21.6–26.5) | 13.0 |
| 0.38 (3.5 metric) | 0.370 (0.345–0.415) 1) | 38.7 (35–42) | 16.5 |
| Polypropylene Monofil Thickness (mm) | | | (for polypropylene) |
| 0.7 metric, 6-0 | 0.100 (0.097–0.103) 2) | 3.3 | 0.7 |
| 1.5 metric, 4-0 | 0.185 (0.175–0.195) 2) | 11.7 | 3.5 |
| 2 metric, 3-0 | 0.25 (0.245–0.28) 2) | 17.3 | 6.5 |
| 3 metric, 2-0 | 0.315 (0.3–0.33) 2) | 22.0 | 12.5 |

1) = Mean values and spread of 5 threads (= 25 measurements).
2) = Mean values and spread of 1 thread (= 4 measurements).

The marked improvement in all values, as regards usage as suture material, of PVDF as compared with PP can readily be seen from the data presented in Table 1. Table 2 also shows additionally the desired value for the knot tear strength for suture material, which desired value is in conformity with the minimum required value of polyamide monofils according to the standard of the European Pharmakopöe.

Figure 1:
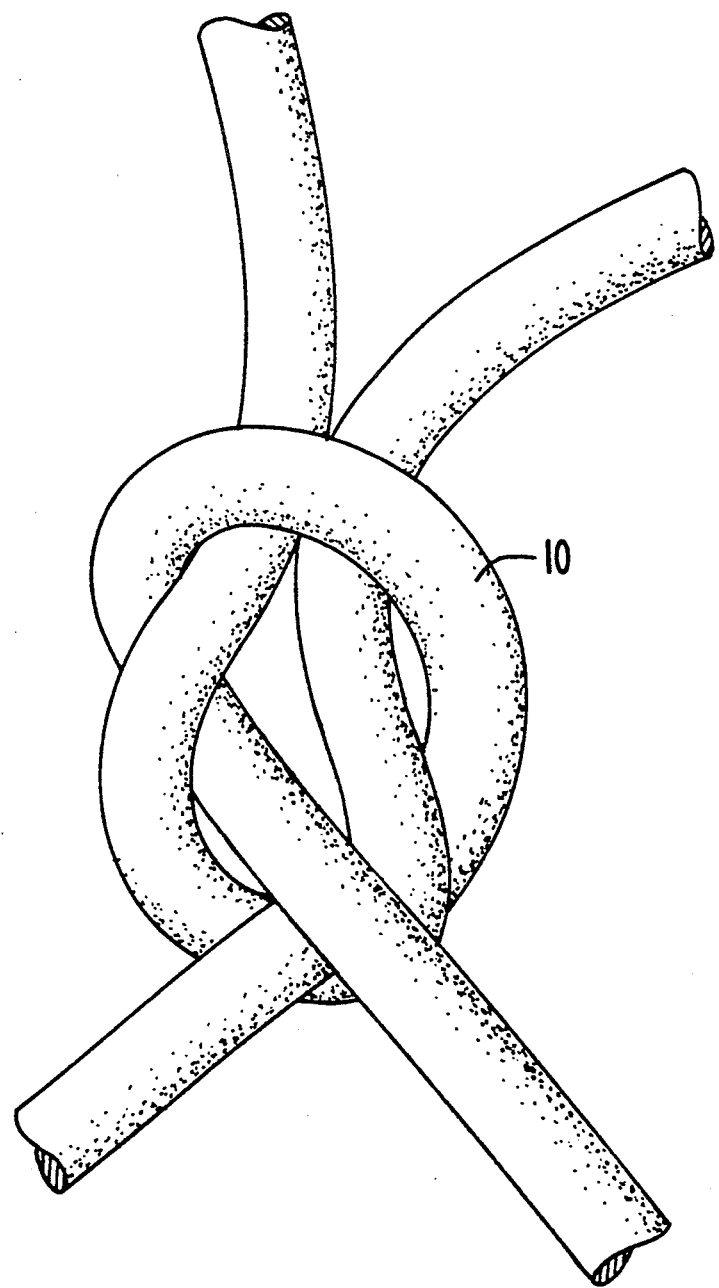
FIG. 1 shows a knot formed of the suture material.
Figure 2:
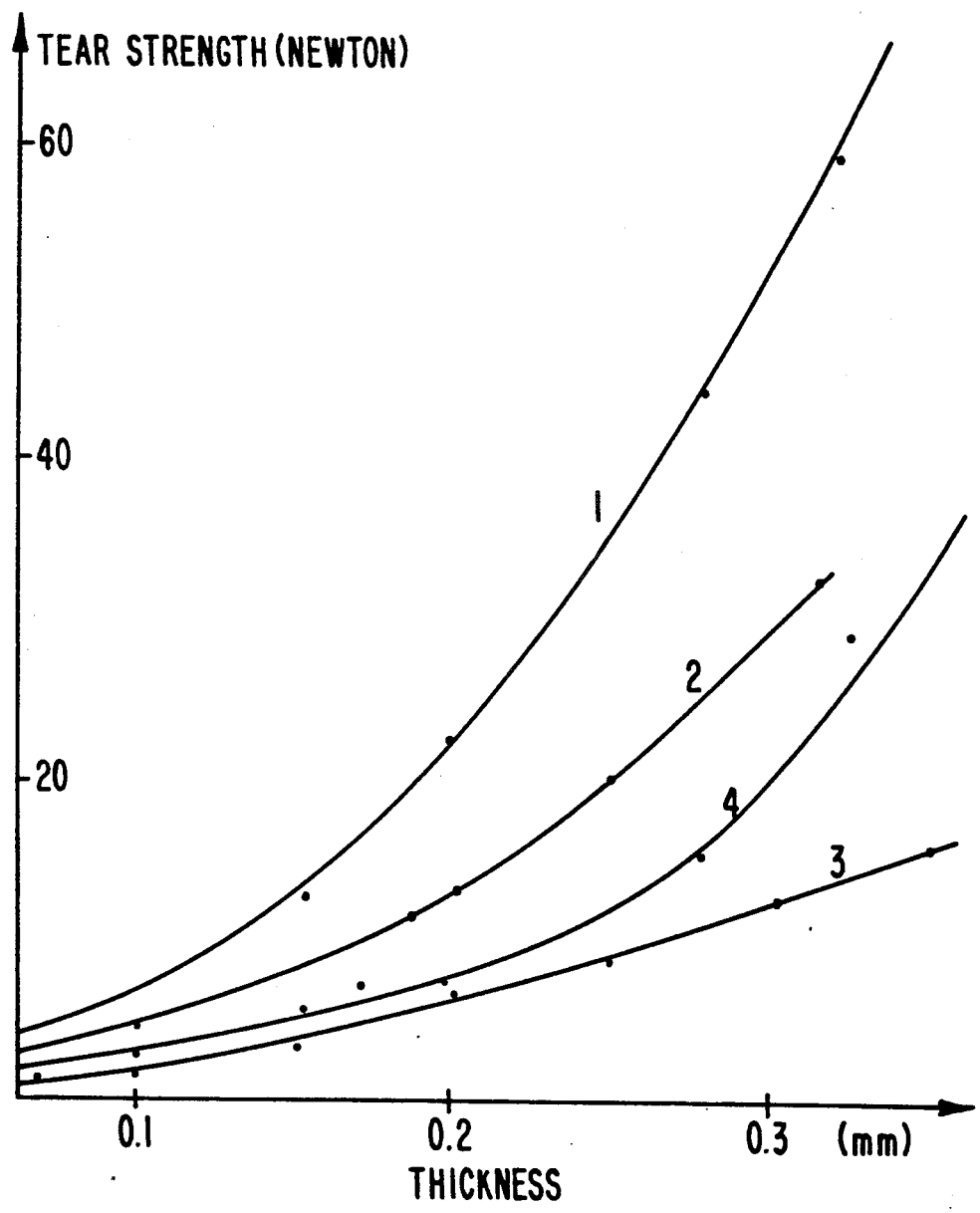
FIG. 2 shows the relationship between the thickness and tear strength of a suture material.

FIG. 2 shows a diagram of tear strengths in dependence on the thickness of the monofil. In this connection, curve 1 shows the tear strength of a PVDF monofil; curve 1a shows the knot tear strength of the PVDF monofil; curve 2 shows the tear strength of a PP monofil, and curve 3 shows the desired value for the knot tear strength, according to the standard of European Pharmakopöe for polyamide monofils. The improvement of the suture material in accordance with the invention is very high.

Table 3 shows the standard of European Pharmakopöe for the minimum knot tear strength of different known sutre materials, measured in Kp.

TABLE 3

Minimum Knot Tear Strength According European Pharmakopöe (kp)

| Thickness metric | Catgut | Silk twisted | Linen twisted | Polyamide monofil | Polyamide twisted | Polyester twisted |
|---|---|---|---|---|---|---|
| 0.3 | 0.010 | — | — | 0.04 | 0.04 | — |
| 0.4 | 0.025 | — | — | 0.05 | 0.05 | — |
| 0.5 | 0.040 | 0.05 | — | 0.08 | 0.08 | 0.10 |
| 0.7 | 0.070 | 0.10 | — | 0.12 | 0.12 | 0.17 |
| 1 | 0.150 | 0.20 | — | 0.14 | 0.20 | 0.20 |
| 1.5 | 0.350 | 0.37 | 0.50 | 0.30 | 0.35 | 0.40 |
| 2 | 0.650 | 0.70 | 0.80 | 0.60 | 0.65 | 0.80 |
| 2.5 | 9.850 | 1.10 | 1.10 | 0.80 | 1.00 | 1.20 |
| 3 | 1.25 | 1.40 | 1.30 | 1.30 | 1.40 | 1.70 |
| 3.5 | 1.60 | 1.85 | 1.75 | 1.65 | 1.80 | 2.23 |
| 4 | 2.25 | 2.30 | 2.20 | 2.00 | 2.20 | 2.90 |
| 5 | 3.00 | 3.50 | 3.50 | 2.70 | 3.50 | 4.00 |
| 6 | 3.75 | 4.00 | 4.50 | 3.50 | 4.50 | 5.00 |
| 7 | 4.75 | 5.00 | 6.00 | 5.00 | 6.00 | 7.00 |
| 8 | 6.25 | 6.50 | 6.80 | — | 7.00 | 9.00 |

What is claimed is:

1. A suture material of a stretched, extruded monofil consisting of polyvinylidene fluoride; said monofil exhibiting a knot elongation at rupture of 8 to 20% and having a diameter ranging between 0.07 and 0.5 mm.

2. A suture material according to claim 1, characterized in that the extruded monofil is stretched in a ration of 1:3 to 1:8.

3. A suture material of a stretched, extruded monofil of a synthetic fluorocarbon resin, characterized in that the fluorocarbon resin consists of polyvinylidene fluoride and the extruded monofil with a diameter of 0.2 to 2 mm is stretched in a ratio of 1:3 to 1:6 to receive a final diameter between 0.07 to 0.5 mm; said monofil exhibiting a knot elongation at rupture of 8 to 20%.

4. A suture material according to claim 1, characterized in that the extruded monofil is stretched at a ratio of 1:3 to 1:6.

5. A suture material according to claim 1, characterized in that the monofil is one that has been extruded at a melt temperature of polyvinylidene fluoride of 240° to 350° C., cooled to a lower temperature of 125° to 145° C., axially stretched at a ratio of 1:3 to 1:6 at said lower temperature and then cooled to room temperature.

6. A suture material according to claim 1 characterized in that the monofil exhibits a knot tear strength of
at least 4,2N by a monofil of 1,5 metric;
at least 7,3N by a monofil of 2,5 metric;
at least 14,4N by a monofil of 3,0 metric;
at least 21,6N by a monofil of 3,0 metric; and
at least 35,0N by a monofil of 3,5 metric 7. A suture material according to claim 1, characterized in that the monofil exhibit a tear strength of at least
12,0N by a monofil of 1,5 metric;
20,7N by a monofil of 2,0 metric;
33,2N by a monofil of 2,5 metric;
55,1N by a monofil of 3,0 metric; and
77,5N by a monofil of 3,5 metric.

8. A suture material according to claim 1, wherein the polyvinylidene fluoride monofil exhibits higher tear strength and lower elongation at rupture as compared with a polypropylene monofil of the same monofil diameter.

* * * * *